United States Patent [19]

Dohm et al.

[11] 4,287,130

[45] Sep. 1, 1981

[54] REACTING OLEFINS WITH OZONE IN A CARBOXYLIC ACID MEDIUM

[75] Inventors: Klaus-Dieter Dohm, Haltern; Peter Hofmann, Marl, both of Fed. Rep. of Germany

[73] Assignee: Chemische Werke Hüls A.G., Marl, Fed. Rep. of Germany

[21] Appl. No.: 191,270

[22] Filed: Sep. 26, 1980

[30] Foreign Application Priority Data

Oct. 19, 1979 [DE] Fed. Rep. of Germany ....... 2942279

[51] Int. Cl.$^3$ .............................................. C07C 75/00
[52] U.S. Cl. .................................... 260/413; 562/543; 562/544
[58] Field of Search ................ 260/406, 413; 562/543, 562/544

[56] References Cited

U.S. PATENT DOCUMENTS

| | | | |
|---|---|---|---|
| 2,475,605 | 7/1949 | Prutton | 562/544 |
| 2,804,473 | 8/1957 | Phillips | 260/502 |
| 2,813,113 | 11/1957 | Goebel et al. | 260/406 |

OTHER PUBLICATIONS

Kirk–Othmer, Encyclopedia of Chemical Technology, vol. 8 (1966), pp. 821–822.
Kirk–Othmer, Encyclopedia of Chemical Technology, vol. 14 (1967), pp. 410–432.

*Primary Examiner*—John F. Niebling
*Attorney, Agent, or Firm*—Wells & Wells

[57] ABSTRACT

The process for reacting olefins with ozone in a carboxylic acid medium using pure oxygen or an oxygenated gas mixture for the ozone production, is improved by recycling the oxygen or the oxygenated gas mixture leaving the ozonizing stage.

The oxygen containing gas leaving the ozonizing stage is:

(a) washed with the carboxylic acid input of the ozonizing stage,
(b) treated with an aqueous solution of an alkalinically reacting substance, and lastly,
(c) dried and fed back to the ozonizer.

5 Claims, 1 Drawing Figure

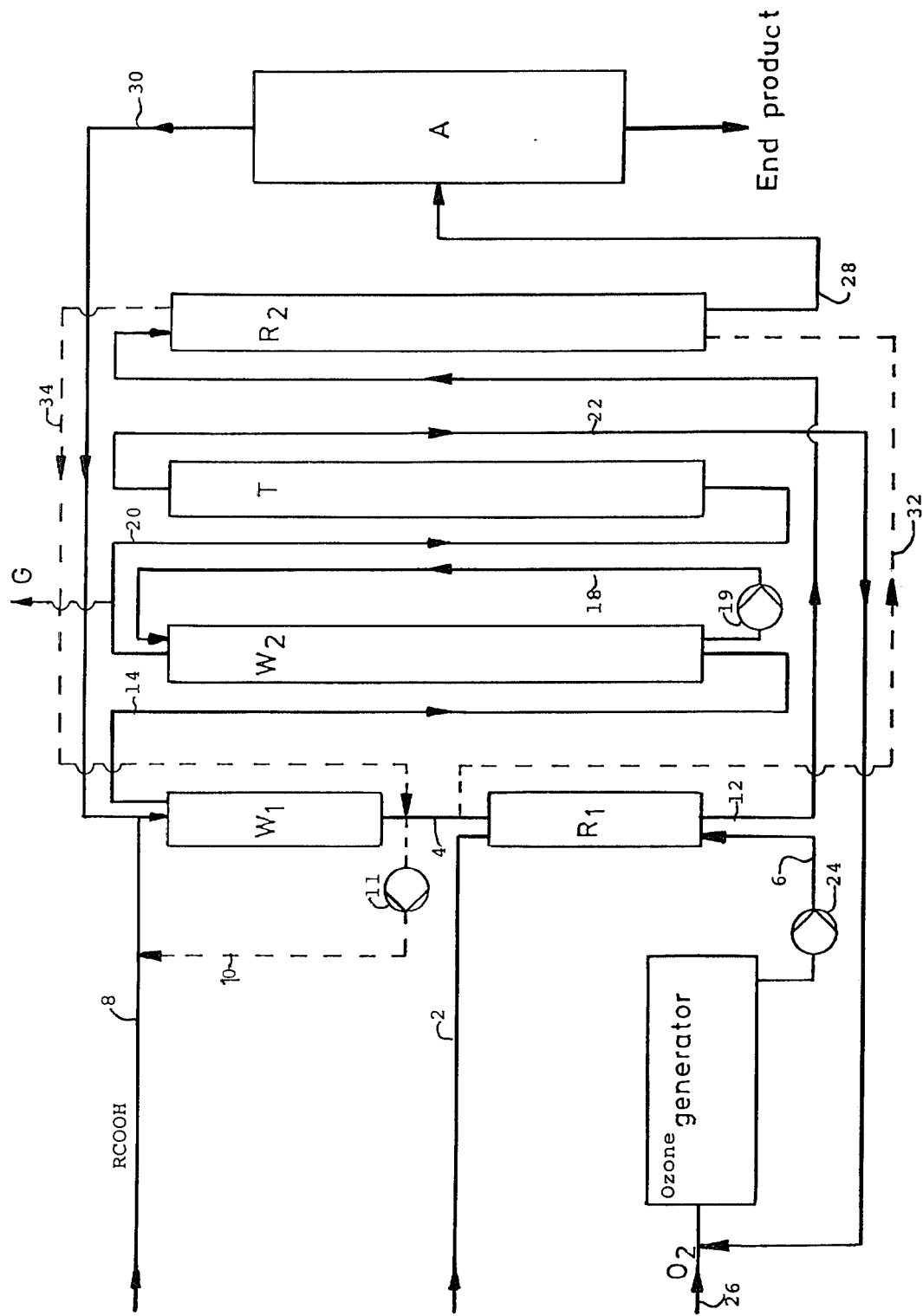

REACTING OLEFINS WITH OZONE IN A CARBOXYLIC ACID MEDIUM

CROSS REFERENCE TO RELATED APPLICATION

Applicants claim priority under 35 USC 119 for application P 29 42 279.5, filed Oct. 19, 1979 in the Patent Office of the Federal Republic of Germany.

BACKGROUND OF THE INVENTION

The field of the invention is ozonolysis and the present invention is particularly concerned with the reaction of olefins with ozone in a carboxylic acid medium.

The state of the art of ozonolysis may be ascertained by reference to the Kirk-Othmer, Encyclopedia of Chemical Technology, 2nd Edition, Vol. 8 (1966) pp. 821–822 and Vol. 14 (1967) under the section OZONE, pp. 410–432, particularly pp. 418–420 where ozonides and ozonide reactions are disclosed, p. 430 where the ozonolysis of oleic acid is disclosed, pp. 421–427 where ozone generation is disclosed, and U.S. Pat. Nos. 2,813,113 and 2,804,473, the disclosures of which are incorporated herein.

The reaction of olefins with ozone (ozonolysis) is known as disclosed in Kirk-Othmer, Vol. 14, pp. 418–419, ibid. In addition to its significance regarding manufacture and analysis, ozonolysis is becoming increasingly important in the chemical industry as a synthetic process. Both linear hydrocarbons and cyclic hydrocarbons with one or more double bonds are suitable as input olefins. For economic reasons, the use of relatively expensive ozone especially for the higher olefins is of interest only for a relatively low specific consumption of ozone per unit mass of the olefin and for a high degree of added value of the end product(s).

Depending on the process, ozonolysis results in peroxidic, aldehydic and/or carboxylic-acidic sequential products or their derivatives (P. S. BAILEY, Chem. Rev. 58, 925, 1958).

As a rule the industrial process does not stop at the stage of the peroxidic ozonolysis products, rather these intermediate products are subjected to a post-treatment in order to obtain stable reaction products. Since the ozonides and di- or oligomeric peroxides most often cannot be converted simply, and then only with a moderate yield into stable end products, the ozonolysis reaction is carried out in so-called participating solvents such as alcohols and carboxylic acids when further reaction of the ozonolysis products is intended. Carboxylic acids are the especially preferred solvents and contrary to the alcohols, they are not attacked by ozone in an oxidizing manner. By further suitably processing by thermolysis, reduction or oxidizing thermolysis the reaction products contained in such solvents, aldehydes, aldehyde/carboxylic-acid mixtures of carboxylic acids are obtained. When cyclic olefins are used, dialdehydes, aldehyde carboxylic acids or dicarboxylic acids are obtained.

Besides air, pure oxygen and mixtures or gases containing oxygen are applicable as the input gas for ozone production. However, even when pure oxygen is used which offers economic advantages over air and mixtures of gases containing oxygen, as much as and more than 90% by volume of the gas used for ozone production remains unutilized. Accordingly, where relatively costly input gases are involved, such as oxygen, oxygen-rich gas mixtures and oxygen-enriched air, there is a problem of economically making use of the practically ozone-free residual gas after the ozonolysis reaction. It is the exception that the residual gas from the ozonolysis is used without further purification for another production run. Even when this is the case, all the shortcomings of two mutually coupled processes arise. Therefore, the preferable approach for utilizing the residual gas is to feed it back, following a pertinent purification, into the ozone production.

Gas purification using electrostatic separation as known from the process of U.S. Pat. No. 2,813,113 is not a generally satisfactory solution. The voltages at which such an apparatus is operated may result in arc formation on account of electric breakdown and hence the oxygenated gas laden with organic substances may ignite. Furthermore, the moisture from humidity introduced with the gas into purification apparatus additionally affects the operational reliability of the electrostatic separators.

SUMMARY OF THE INVENTION

Having in mind the limitations of the prior art, it is an object of the present invention to improve upon the process of reacting olefins with ozone in a carboxylic acid medium by purifying the flow of gas leaving the ozonolysis stage so that it can be fed back to the ozone generator.

This object is accomplished according to the present invention wherein olefins are reacted with ozone in a carboxylic acid medium using oxygen or an oxygenated gas mixture for the ozone production and the oxygen containing gas leaving the ozonizing stage is processed by:

(a) washing the oxygen containing gas with the carboxylic acid input of the ozonizing stage;

(b) treating the carboxylic acid washed oxygen containing gas with an alkalinically reacting substance; and (c) drying the treated gas and feeding the dry oxygen containing gas back to the ozonizer.

BRIEF DESCRIPTION OF THE DRAWING

The FIGURE of the drawing is a flow sheet showing the apparatus and process stages of the present invention.

DESCRIPTION OF THE PREFERRED EMBODIMENTS

The olefins used in the process of the present invention can be both linear and cyclic and can be simple or polyunsaturated hydrocarbons. For reasons of safety, olefins having less than 5 C atoms are not to be used. As a rule olefins having 6 to 30, preferably 8 to 24 C atoms are used. Typical of the series of linear and cyclic olefins are for instance alpha-olefins having C numbers from 12 to 18, such as oleic acid, elaidic acid, erucic acid, cyclooctene, cyclododecene, cyclooctadiene and cyclododecatriene.

Suitable carboxylic acids useful in the present invention have up to 12 C atoms. However, those monocarboxylic acids are preferred which have 1 to 4 C atoms, for instance, formic acid, acetic acid and propionic acid. Acetic acid and propionic acid are preferred because they have less corrosiveness than that of formic acid, because of their cheap availability and their advantageous dissolving power and boiling points. When appropriate for carrying out the process of the present invention, carboxylic acid anhydrides may also be used in addition to the carboxylic acids.

As a rule, the carboxylic acid(s) is (are) used in at least equimolar amounts with respect to the olefin. The use of olefinic raw materials which bear one or more carboxyl groups makes possible the use of less than molar amounts of carboxylic acids (down to as little as approximately 0.5 moles of carboxylic acid per mole of olefin). It is suitable, however, to use from 2 to 20 units by weight of carboxylic acid per unit weight of olefin.

Applicable raw material gases for the production of ozone are air, oxygenated gas mixtures, for instance, mixtures with nitrogen, argon and carbon dioxide containing at least 20% by volume of oxygen. The ozone concentration used is about 0.01 to 10% by volume.

The following table gives examples of the overall combination of olefin starting material, carboxylic acid medium, ozone concentration and end product as processed according to the present invention.

| Olefin | RCOOH | Ozone Concentration % by volume | End Product |
|---|---|---|---|
| cyclododecene | propionic acid | 2.41 | dodecanedioic acid |
| cyclododecene | acetic acid | 2,00 | dodecanedioic acid |
| cyclododecene | acetic acid | 1,00 | dodecanedioic acid |
| cyclododecene | acetic acid | 0,50 | dodecanedioic acid |
| cyclooctene | propionic acid | 2,50 | octanedioic acid |
| cyclooctene | acetic acid | 1,00 | octanedioic acid |
| oleic acid | acetic acid | 1,00 | pelargonic acid + nonanedioic acid |
| oleic acid | propionic acid | 1,00 | pelargonic acid + nonanedioic acid |
| oleic acid | pelargonic acid | 1,00 | pelargonic acid + nonanedioic acid |
| dodecene-1 | propionic acid | 1,00 | undecanoic acid |

The process of the present invention is explained in further detail below with reference to the FIGURE of the drawing.

A mixture of olefin from line 2 and carboxylic acid from line 4 is exposed to the ozone-containing gas flow from line 6 in a first reaction stage $R_1$. The reactor $R_1$ is for instance an agitated vessel having a gas intake conduit dipping into the liquid. Apparatus permitting complete conversion both of the olefin and the ozone is for instance a bubble column or a trickling tower reactor in which a gas (from line 6 below) or a liquid (from lines 2 and 4 above) respectively are passed in counterflow and such apparatus is especially advantageous.

In a first purification or wash stage $W_1$, the ozone-free or at least largely ozone-free exhaust gases rising through line 4 are washed with the carboxylic acid entering from line 8 used as the solvent for the olefin, with a carboxylic acid anhydride or with a mixture of carboxylic acid and carboxylic acid anhydride.

The discharge from the first washing stage $W_1$ then is fed through line 4 to the ozonolysis reactor $R_1$. A suitable purification stage $W_1$, for instance, is a trickling tower and the gas to be purified is fed in counterflow through line 4 from below to the washing liquid from line 8. When the input of carboxylic acid used as solvent for the ozonolysis suffices to ensure effective gas purification for a simple passage through the washing column $W_1$, there is no need for operating the washing liquid from line 8 in the closed circuit 10 shown in dotted lines and pump 11. When circulation, however, is required to increase the liquid flow rate in the first purification stage $W_1$, then the input into the washing circuit is controlled so that the withdrawal of solvent for the ozonolysis reaction $R_1$ through line 12 and the losses due to entraining in the gas flow are compensated.

The exhaust gas leaving the first purification stage $W_1$ through line 14 appropriately is partly freed by condensation prior to another wash, in order to minimize the loss of wash with high vapor pressures, from its organic components. This is implemented for instance, in that the gas is cooled to a temperature above the solidification point of the wash used in stage $W_1$, whereby the organic components are partly recovered as a liquid condensate.

The gas, pretreated or not, then arrives at the second purification stage $W_2$ from line 14 where it is freed from the solvent or solvent residues from the first stage $W_1$. The second washing liquid introduced from line 18 is at least 0.1% by weight of aqueous solutions of alkalinically reacting substances such as hydroxides, carbonates and bicarbonates of alkali or earth-alkali metals. Typical substances are NaOH, KOH, $Na_2CO_3$ and $NaHCO_3$. When gas mixtures containing carbon dioxide are used for the production of ozone, solutions of bicarbonates are appropriately employed as a washing medium.

The washing procedure in the second purification stage $W_2$ is carried out, for instance, so that the gas is fed through line 14 from below into a trickling tower, bubble column or a bubble tray column in counterflow to the circulating washing liquid pumped through line 18 by pump 19.

The exhaust gas leaving the second purification stage $W_2$, through line 20 appropriately is freed as much as possible from any entrained water vapor in order to minimize the load on the subsequent drying procedure. Here as for the first purification stage $W_1$, the procedure is the same as for the cooling system behind the stage.

In the third purification stage T the exhaust gas lastly is rid of moisture by suitable drying procedures down to a dew point less than or equal to $-20°$ C., preferably, however, less than or equal to $-50°$ C. The dessicant can be arranged in towers where the gas flows through it. Suitable dessicants are, for instance $CaCl_2$, $NaSO_4$, $P_2O_5$ and silica gel. When proceeding commercially, preferably a molecular sieve of suitable pore size is used, as thereby simple regeneration is possible. To ensure continuous operation of the ozone generator, two drying units connected in parallel are appropriately operated in alternation.

The gas separated from organic substances and humidity now can be introduced through line 22 into the ozone generator of a conventional design as disclosed in Kirk-Othmer, ibid., Vol. 14, pp. 421–427 for the purpose of renewed ozone production. To maintain circulation of the gas and overcome the counterpressure building up in the apparatus, the gas is compressed by a suitable compressor or blower 24. In order to minimize the presence of inorganic components (for instance $N_2$, Ar, $CO_2$, etc.), these components are tapped out of the gas circulation line 20 (gas tap G). To replace these gas losses and also to make up for the oxygen used for ozone production, fresh gas is steadily supplied through line 26.

The liquid reaction mixture leaving the ozonolysis stage $R_1$ through line 12 as a rule is converted in a posttreatment stage $R_2$, either by reduction, thermolytically or by combined oxidation and thermolysis into stable end products. When the post-treatment is completed, the reaction mixture is passed through line 28, reprocessed in stage A and the solvent so recovered is fed back through line 30 as a washing medium into the first purification stage $W_1$.

The following variations in procedure are possible embodiments of the post-treatment $R_2$ by oxidation/-thermolysis:

(1) The ozonolysis mixture from line 12 is oxidized in $R_2$ at a high temperature up to 150° C. depending on the treatment with an oxygenated gas mixture of a different composition than the input gas used for ozone production or the exhaust gas from the ozonolysis stage by way of dotted line 32. In this case, the post-treatment stage may be provided with its own gas circuit and possibly with suitable purification stages. When the gas used for the post-oxidation is air, gas-feedback by way of dotted line 34 can be eliminated.

(2) The ozonolysis mixture from line 12 is post-treated in $R_2$ in oxidizing manner again at high temperature with part of the exhaust gas from the ozonolysis stage admitted through line 32. The exhaust gas leaving the post-treatment stage following condensation of the organic components is fed back by line 34 to the gas circuit of the ozonolysis of the first purification stage $W_1$.

To replace the oxygen used up in the post-treatment, an increased amount of fresh gas is fed to the ozonolysis gas circuit through line 6. When the oxygen of the gas used for post-treatment is extensively or entirely converted, then the exhaust gas from the post-treatment stage passing through dotted line 34 is eliminated from being fed into the ozonolysis gas circuit. In such a case, tapping a side flow from the ozonolysis gas circuit to remove inorganic components ($N_2$, Ar, $CO_2$, etc.) at G is superfluous.

The process of the present invention is commercially applicable to all ozonolysis procedures which are carried out in a carboxylic acid medium.

Unless otherwise indicated, all percentages below are by weight.

The example below serves to further explain the process of the present invention.

EXAMPLE

166 Parts by weight of cyclododecene an hour are loaded through line 2 into the ozonolysis reactor $R_1$. Furthermore, 830 parts by weight of propionic acid an hour are fed through line 8, the first purification stage $W_1$ and line 4 into the ozonolysis reactor $R_1$. A flow of oxygen containing 2.41% by volume of ozone with 48 parts of ozone per hour is passed through line 6 from below through the trickle-tower-ozonolysis-reactor $R_1$, water-cooled to a temperature of 20° C. in counterflow to the liquid components of the reaction mixture entering through lines 2 and 4. The reaction is noticeable in the reactor bed of $R_1$ by a temperature rise of about 20° C. and is controlled so that the reaction zone is always about at the center of the ozonolysis reactor. Complete conversion of olefin and ozone is ensured in this manner. The liquid reaction mixture drains continuously through line 12 and is fed to an oxidizing-thermolytic post-treatment reactor $R_2$.

The presently ozone-free oxygen leaving the ozonolysis reactor through line 4 then is washed in a trickling tower $W_1$ with 830 parts by weight of propionic acid an hour entering line 8. The dwell time of the propionic acid in the trickling tower $W_1$ is 2.5 hours for a cross-sectional load of 66.4 $g/cm^2 \cdot h$ of propionic acid. The content is $C_{12}$ compounds and shorter chain decomposition products in the exhaust gas through line 14 of the purification stage all together is less than 1 ppm.

After the first purification stage, the gas flow is freed, by condensation at a cooling temperature of $-18°$ C., to such an extent from propionic acid that only about 3 parts by weight/hr of propionic acid are discharged through line 14, which then are removed by counter-flow washing with 10% soda liquor in $W_2$. By pumping a circulatory flow of soda liquor of 60,000 parts by weight an hour in $W_2$ and by observing a dwell time of 15 minutes and a cross-sectional load of 1,200 $g/cm^2 \cdot hr$ of soda liquor, it is possible to wash the propionic acid out of the exhaust gas to values less than 0.5 ppm leaving line 20.

The gas so purified is predried by sol cooling ($+5°$ C.) and then is rid of moisture in a drying column T filled with a commercial molecular sieve down to a dew point $< -50°$ C. The loading of the drying column through line 20 is 62 liters of gas per liter of dessicant an hour.

By feeding fresh gas through line 26 with an $O_2$ content greater than 99.5% by volume to replenish that used up in the reaction or lost through the tap G, the gas is reintroduced into the ozone generator through line 22 operating on the Siemens ozonizer tube principle. After leaving the ozonizer, the ozone-containing oxygen is compressed by compressor 24 to overcome the counter-pressure present in the apparatus.

The ozonlysis mixture leaving $R_1$ through line 12, after addition of 200 parts water, is post-treated in oxidizing-thermolytic manner in reactor $R_2$ designed as a bubble column. The dwell time of the input mixture into $R_2$ is 10 hours for a cross-sectional load of 24 $g/cm^2 \cdot hr$ of liquid. Three different temperature levels are set by three separate heating or cooling zones in the bubble reactor $R_2$: the upper third is at 70° C., the center third is at 90° C., and the lower third is at 100° C. 5% of the exhaust gas from the ozonolysis stage are fed through line 32 as oxidizing means in counterflow to the input mixture fed through line 12 in at the top. The exhaust gas leaving the bubble column through line 34 after extensive condensation of the organic components is fed back into the ozonolysis circuit before the first purification stage $W_1$.

The reaction mixture leaving the post-treatment reactor through line 28 is cooled. The raw product so obtained is filtered. The residue obtained after concentrating the filtrate in A is combined with the raw product and recrystallized in propionic acid. The dodecanoic acid is obtained in a yield of 83% and a purity of 99% as end product.

We claim:

1. In a method for reacting ozone with olefins in a carboxylic acid medium in an ozonizing stage where an oxygen-containing gas is passed through an ozone production stage to produce said ozone and the oxygen-containing gas leaving said ozonizing stage is recycled, the improvement comprising:
    (a) washing said oxygen-containing gas leaving said ozonizing stage with said carboxylic acid;
    (b) treating the gas leaving step (a) with an aqueous solution of an alkalinically reacting substance; and
    (c) drying the gas leaving step (b) and recycling the dried gas to said ozone production stage.

2. The method of claim 1, further comprising a condensation after step (a).

3. The method of claim 2, further comprising a condensation after step (b).

4. The method of claim 1, wherein the reaction products of said ozonizing stage are treated with a portion of said oxygen-containing gas leaving said ozonizing stage.

5. The method of claim 4, wherein said portion is recycled and introduced after step (a).

* * * * *